United States Patent [19]
Gribou

[11] Patent Number: 4,960,591
[45] Date of Patent: Oct. 2, 1990

[54] METHODS AND COMPOSITIONS FOR RELIEF OF STOMACH DISTRESS

[76] Inventor: Henry G. Gribou, 3565 S. Oakdale Dr., New Berlin, Wis. 53151

[21] Appl. No.: 338,942

[22] Filed: Apr. 17, 1989

[51] Int. Cl.$^5$ .................... A61K 37/00; A61K 33/00
[52] U.S. Cl. ........................................ 424/93; 424/717
[58] Field of Search .................... 424/715, 717, 93; 514/164

[56] References Cited

U.S. PATENT DOCUMENTS

| | | | |
|---|---|---|---|
| 3,278,312 | 10/1966 | Griffon et al. | 424/93 |
| 3,608,064 | 9/1971 | Lamb | 424/439 |
| 4,003,989 | 1/1977 | Bar-On | 514/164 |
| 4,590,077 | 5/1986 | Trop | 426/61 |
| 4,595,590 | 6/1986 | Hublot et al. | 424/93 |
| 4,617,190 | 10/1986 | Montgomery | 426/61 |
| 4,766,076 | 8/1988 | Sandine et al. | 435/253.6 |

*Primary Examiner*—Douglas W. Robinson
*Assistant Examiner*—Kevin Weddington
*Attorney, Agent, or Firm*—Rogers, Howell & Haferkamp

[57] ABSTRACT

A method for relief of stomach distress is disclosed. The method comprises ingestion of a composition comprising non-fat dry milk and sodium bicarbonate. Compositions in particulate or tablet form for relief of stomach distressd comprising non-fat dry milk and sodium bicarbonate are also disclosed.

12 Claims, No Drawings

METHODS AND COMPOSITIONS FOR RELIEF OF STOMACH DISTRESS

BACKGROUND OF THE INVENTION

1. Field of the Invention

The present invention relates to relief of stomach distress, and more particularly to relief of stomach distress by ingestion of an antacid.

2. Description of the Prior Art

Stomach distress, especially that caused by excess stomach acid, is a very common ailment and many products are commercially available for its relief. Yet, such commercial remedies also have several drawbacks.

Conventional remedies currently available on the market comprise aluminum hydroxide, magnesium hydroxide, calcium carbonate, or a combination thereof as an antacid. However, such ingredients have been associated with several undesirable side effects. Aluminum hydroxide has been reported to cause constipation, and it has been suggested that adults suffering from metabolic bone diseases should avoid aluminum-containing antacids. Those suffering from kidney disease also have been advised against ingestion of aluminum hydroxide over long periods o time. Moreover, some reports have linked aluminum ingestion with Alzheimer's disease.

Magnesium hydroxide also has been associated with health problems. Since magnesium hydroxide is a laxative, it has a tendency to cause diarrhea and should not be used regularly. Further, magnesium-containing antacids should be avoided by those with severe kidney disease. In fact, it is recommended that such antacids not be taken for more than two weeks without strict medical supervision. The constipation-inducing effect of aluminum hydroxide might be counteracted by the laxative effect of magnesium hydroxide in an antacid employing a combination of the two, but the two often are not counterbalanced so precisely as to completely nullify the effects. Thus, ingesting even those antacids comprising a combination of aluminum hydroxide and magnesium hydroxide tends to cause either constipation or diarrhea.

Ingestion of calcium carbonate has been related to constipation. In addition, its use is not recommended by those with high blood calcium levels, reduced parathyroid gland function, kidney stones or irregular heart beat.

Accordingly, safe antacids are still needed that avoid the use of aluminum hydroxide, magnesium hydroxide and calcium carbonate, and the side effects associated with such compounds.

SUMMARY OF THE INVENTION

Briefly, therefore, the present invention is directed to a novel method for relief of stomach distress. The method comprises ingestion of a composition comprising non-fat dry milk and sodium bicarbonate.

The present invention is also directed to a novel composition for relief of stomach distress comprising non-fat dry milk and sodium bicarbonate. The composition is in particulate form.

The present invention is further directed to such composition that is in tablet form, and to a novel method for preparation of a composition for relief of stomach distress. The method comprises compressing a mixture comprising non-fat dry milk and sodium bicarbonate into tablet form.

Among the several advantages found to be achieved by the present invention, therefore, may be noted the provision of a method for relief of stomach distress that does not require ingestion of aluminum hydroxide, magnesium hydroxide or calcium carbonate; the provision of such method that is less likely to produce the side effects associated with such ingredients; the provision of a composition for relief of stomach distress; and the provision of a method for preparation of such composition.

DESCRIPTION OF THE PREFERRED EMBODIMENTS

In accordance with the present invention, it has been discovered that ingestion of a composition comprising non-fat dry milk and sodium bicarbonate can relieve stomach distress associated with excess stomach acid. This composition provides a surprisingly effective aid in relieving stomach distress—one far more effective than non-fat dry milk or sodium bicarbonate individually. Moreover, such relief can be attained without ingestion of aluminum hydroxide, magnesium hydroxide or calcium carbonate. The risk of side effects associated with ingestion of such ingredients may thereby be reduced.

Generally, the composition of this invention may be prepared simply by mixing together non-fat dry milk and sodium bicarbonate. Although buffers other than or in addition to sodium bicarbonate might be considered, sodium bicarbonate is particularly suitable because of the drawbacks of many other buffers, as discussed above, and because it is recognized as gentle to the digestive system. The particular proportions of the ingredients are not considered to be vital, but it has been found that the bulk of the composition generally should be non-fat dry milk. Preferably, the composition comprises less than about 2 parts by weight yeast and about 2 to about 10 parts by weight, or more preferably about 2 to about 6 parts by weight sodium bicarbonate per 100 parts by weight non-fat dry milk. A typical weight ratio of non-fat dry milk to sodium bicarbonate would be in the neighborhood of about 50:1, although a wide range of proportions is contemplated.

The ingredients can be used in almost any form, although particulate or aqueous solution forms are especially suitable. It is especially desirable that the nonfat dry milk and the sodium bicarbonate be in particulate form and be mixed by any conventional means. If desired, yeast may also be added. Although any proportion might be acceptable, it is particularly desirable that the yeast be incorporated into the composition in an amount of no more than about the amount of sodium bicarbonate, by weight. As with the other ingredients, the yeast may be added in any form, although a particulate form is most desirable. Other additives, such as flavoring agents or coloring agents, may also be added.

If the ingredients are of particulate form, the mixture produced therefrom may be ingested directly as a particulate mixture, placed into capsules or, preferably, compressed into tablet form. The mixture may be ingested by any of the usual methods, including, swallowing, chewing and swallowing or dispersing or dissolving in a liquid such as water and drinking. If the mixture is a liquid, it may be ingested by drinking it at full strength or in a diluted form.

It has been found that combining non-fat dry milk with sodium bicarbonate provides a surprisingly effective aid in relieving stomach distress. It has been found that ingestion of sodium bicarbonate alone induces an undesirably rapid pH change in the stomach. However, the inclusion of the milk not only helps slow the pH change, but also serves to soothe and possibly coat the stomach or other portions of the digestive system. Moreover, addition of yeast has been found to produce somehow an even superior distress-relieving action.

The following example describes a preferred embodiment of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE

A stomach relief distress composition was prepared by mixing together non-fat dry milk (960 gms.), sodium bicarbonate (20 gms.) and yeast (20 gms.).

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed:

1. A method for relief of stomach distress, comprising ingestion of a composition comprising non-fat dry milk, yeast and sodium bicarbonate.
2. A method as set forth in claim 1 wherein said composition further comprising a flavoring agent.
3. A method as set forth in claim 1 wherein said composition is in particulate form.
4. A method as set forth in claim 1 wherein said composition is in the form of a tablet.
5. A method as set forth in claim 3 wherein said composition is in particulate form.
6. A method as set forth in claim 3 wherein said composition is in the form of a tablet.
7. A method as set forth in claim 3 wherein said composition is ingested by mixing said composition with water to form an aqueous mixture and drinking the mixture.
8. A method as set forth in claim 5 wherein said composition is ingested by mixing said composition with water to form an aqueous mixture and drinking the mixture.
9. A composition for relief of stomach distress comprising non-fat dry milk, yeast and sodium bicarbonate, said composition being in particulate form.
10. A composition as set forth in claim 9, further comprising a flavoring agent.
11. A composition for relief of stomach distress comprising non-fat dry milk, yeast and sodium bicarbonate, said composition being in tablet form.
12. A composition as set forth in claim 11, further comprising a flavoring agent.

* * * * *